US010137744B2

(12) United States Patent
Heuermann et al.

(10) Patent No.: US 10,137,744 B2
(45) Date of Patent: Nov. 27, 2018

(54) MEASUREMENT AND MONITORING DEVICE FOR TIRE-RELATED VARIABLES OF A VEHICLE

(71) Applicant: Fachhochschule Aachen, Aachen (DE)

(72) Inventors: Holger Heuermann, Aachen (DE); Thomas Harzheim, Eschweiler (DE)

(73) Assignee: Fachhochschule Aachen, Aachen (DE)

( * ) Notice: Subject to any disclaimer, the term of this patent is extended or adjusted under 35 U.S.C. 154(b) by 0 days.

(21) Appl. No.: 15/544,954

(22) PCT Filed: Jan. 19, 2016

(86) PCT No.: PCT/DE2016/100021
§ 371 (c)(1),
(2) Date: Jul. 20, 2017

(87) PCT Pub. No.: WO2016/116098
PCT Pub. Date: Jul. 28, 2016

(65) Prior Publication Data
US 2017/0368892 A1    Dec. 28, 2017

(30) Foreign Application Priority Data

Jan. 22, 2015  (DE) ........................ 10 2015 100 890

(51) Int. Cl.
*B60C 23/04*    (2006.01)
*B60C 11/24*    (2006.01)
(Continued)

(52) U.S. Cl.
CPC .......... *B60C 23/0444* (2013.01); *B60C 11/24* (2013.01); *B60C 11/243* (2013.01);
(Continued)

(58) Field of Classification Search
CPC ..... B60C 11/24; B60C 11/243; B60C 11/246; B60C 23/00; B60C 23/02; B60C 23/04;
(Continued)

(56) References Cited

U.S. PATENT DOCUMENTS 3,873,965 A * 3/1975 Garcia ................ B60C 23/0433
200/61.25
5,216,372 A * 6/1993 Zoughi .................. G01B 15/02
324/638
(Continued)

FOREIGN PATENT DOCUMENTS

DE    2461212 A1   10/1975
DE    4326976 A1   2/1995
(Continued)

OTHER PUBLICATIONS

International Search Report dated Jun. 15, 2016, in International Application No. PCT/DE2016/100021.
(Continued)

*Primary Examiner* — Andrew W Bee
(74) *Attorney, Agent, or Firm* — Stephan A. Pendorf; Patent Central LLC

(57) ABSTRACT

A device for measuring and/or monitoring tire-related variables of a vehicle, having a sensor unit for transmitting, receiving and processing signals, wherein a transmission signal is emitted by an antenna unit of the sensor unit in the direction of an object being measured and wherein a reflection signal reflected by the object being measured is received and analyzed, the sensor unit having a transceiver device, via which a reflection factor, formed as the quotient from the reflection signal reflected by the object being measured and the transmission signal, is measured and via which a resonance frequency and/or a phase difference between the transmission signal and the reflection signal is determined, wherein the transceiver unit comprises a vector network (Continued)

Figure 1:
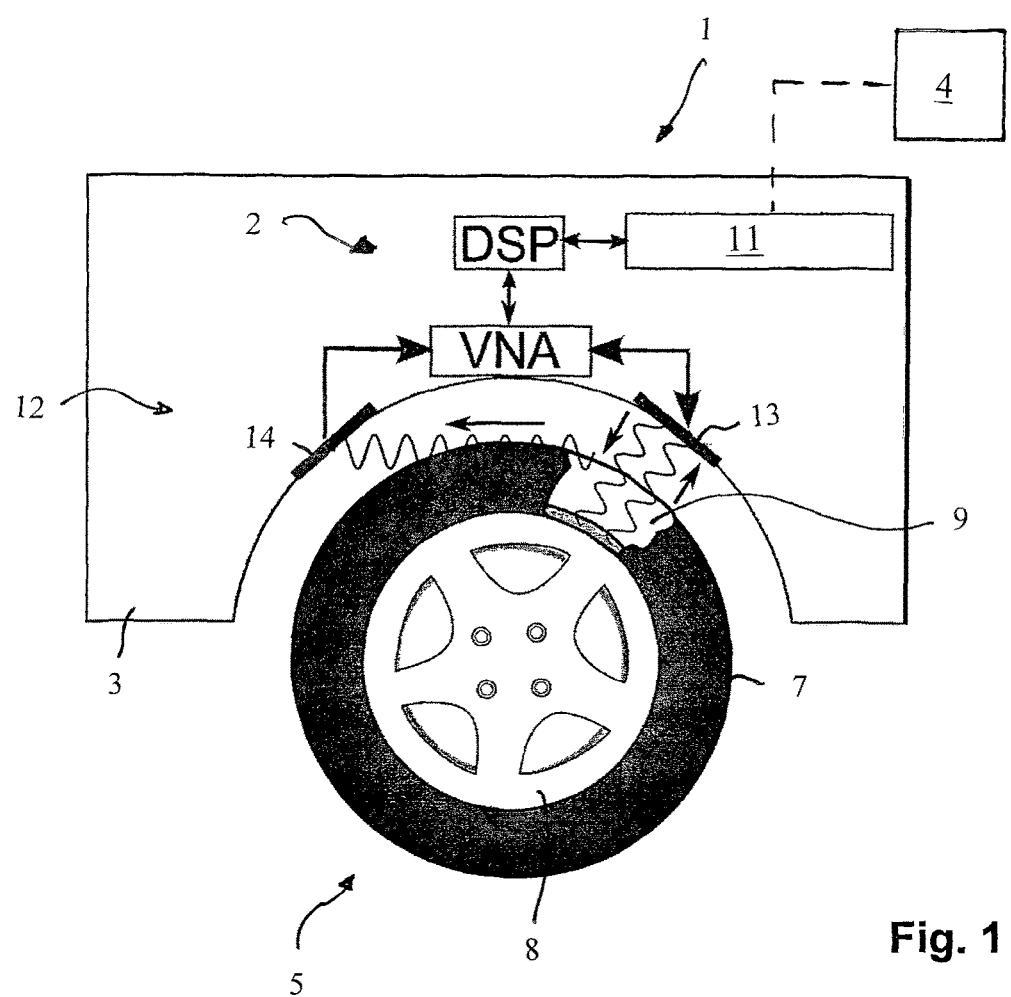

analyzer and an analysis unit, so that a distance to the object being measured is established by detecting the phase difference between the transmission signal and the reflection signal.

10 Claims, 6 Drawing Sheets

(51) Int. Cl.
| | |
|---|---|
| B60C 23/02 | (2006.01) |
| B60C 23/00 | (2006.01) |
| G01M 17/02 | (2006.01) |
| G01S 7/02 | (2006.01) |
| G01S 7/35 | (2006.01) |
| G01S 7/40 | (2006.01) |
| G01R 27/28 | (2006.01) |
| G01S 13/36 | (2006.01) |
| G01S 13/88 | (2006.01) |
| G01N 22/00 | (2006.01) |
| H01Q 1/22 | (2006.01) |
| G01L 17/00 | (2006.01) |
| G01S 13/75 | (2006.01) |

(52) U.S. Cl.
CPC ............ *B60C 11/246* (2013.01); *B60C 23/00* (2013.01); *B60C 23/02* (2013.01); *B60C 23/04* (2013.01); *B60C 23/0408* (2013.01); *B60C 23/0416* (2013.01); *B60C 23/0422* (2013.01); *B60C 23/0428* (2013.01); *B60C 23/0433* (2013.01); *B60C 23/0435* (2013.01); *G01L 17/00* (2013.01); *G01M 17/02* (2013.01); *G01N 22/00* (2013.01); *G01R 27/28* (2013.01); *G01S 7/025* (2013.01); *G01S 7/354* (2013.01); *G01S 7/4017* (2013.01); *G01S 13/36* (2013.01); *G01S 13/88* (2013.01); *H01Q 1/2241* (2013.01); *G01S 13/753* (2013.01); *G01S 2007/4039* (2013.01)

(58) Field of Classification Search
CPC ............ B60C 23/0408; B60C 23/0422; B60C 23/0433; B60C 23/0435; B60C 23/0444
See application file for complete search history.

(56) References Cited

U.S. PATENT DOCUMENTS

| | | | |
|---|---|---|---|
| 2002/0189336 | A1 | 12/2002 | McEwan |
| 2008/0238644 | A1* | 10/2008 | Voigtlaender ........... B60C 23/06 340/443 |
| 2010/0060434 | A1* | 3/2010 | Shiotsu .............. G06K 19/0707 340/10.51 |

FOREIGN PATENT DOCUMENTS

| | | | |
|---|---|---|---|
| DE | 102009013458 A1 | | 9/2010 |
| WO | 4117158 A1 | | 11/1992 |
| WO | 03/027709 | * | 4/2003 |
| WO | 03027709 A1 | | 4/2003 |
| WO | 2010120558 A2 | | 10/2010 |

OTHER PUBLICATIONS

Written Opinion of the International Search Authority in International Application No. PCT/DE2016/100021 dated Jun. 15, 2016.

\* cited by examiner

MEASUREMENT AND MONITORING DEVICE FOR TIRE-RELATED VARIABLES OF A VEHICLE

The invention relates to a device for measuring and/or monitoring tire-related variables of a vehicle, comprising a sensor unit for transmitting, receiving and processing signals, wherein a transmission signal can be emitted by an antenna unit of the sensor unit in the direction of an object being measured and wherein a reflection signal reflected by the object being measured can be received and analysed, the sensor unit comprises a transceiver device, by means of which a reflection factor, formed as the quotient from the reflection signal reflected by the object being measured and the transmission signal, can be measured and by means of which a resonance frequency and/or a phase difference between the transmission signal and the reflection signal can be determined.

From DE 2461212 A1 a device for measuring the pressure of tires of a vehicle is known, comprising a transceiver unit with an oscillator for generating a transmission signal in a microwave frequency range. The transceiver unit further comprises an antenna unit, via which the transmission signal can be emitted in the direction of a compressible object being measured arranged on a rim well of a wheel. The transceiver unit further comprises an analysis unit and a receiving antenna, so that when the compressible object being measured expands the change in frequency of a reflection signal can be detected. The compressible object being measured has a section able to extend as a function of the air pressure of the tire, leading to a change in the frequency of the reflection signal and in this way allowing a change in the tire pressure to be derived. The disadvantage of the known device is that the susceptibility to failure due to changing environmental conditions is relatively high.

From DE 102009013458 A1 a device for measuring and/or monitoring tire-related variables of a vehicle is known, comprising a sensor unit with a transceiver unit and an analysis and antenna unit. A transmission signal is emitted by the antenna unit in the direction of an object being measured. Based on a beam reflected by the object being measured the distance of the object being measured from the antenna unit can be concluded. To this end the ratio of the transmitted power to the reflected power is formed. This does not allow the current state of the object being measured to be detected.

The object of the present invention is therefore to further develop a device for measuring and/or monitoring tire-related variables of a vehicle such that a measurement of vehicle-related variables, particularly the tire pressure, that is accurate and stable over time, is guaranteed.

To achieve this object the invention, in conjunction with the characterising part of claim 1, is characterized in that the transceiver unit has a vector network analyser and an analysis unit, so that distance to the object being measured can be established by detecting the phase difference between the transmission signal and the reflection signal.

According to the invention a vector network analyser (VNA) is provided, by means of which an inexpensive and robust monitoring or measurement of objects being measured is guaranteed. Advantageously, a plurality of measured variables can be detected with one and the same measurement. The measured data transmission takes place within a matter of microseconds. The device according to the invention also has low weight.

According to a further development of the invention, the network analyser can be used to detect the tire pressure, the speed of rotation, the steering angle, the compression depth, the humidity of the road and metal foreign bodies in the tire.

According to a further development of the invention, the transceiver unit is arranged in a wheel arch of a vehicle. The object being measured is configured as a compressible structural element, arranged inside an interior space delimited by a tire and a rim of the wheel in the peripheral direction of the wheel. The antenna unit of the transceiver unit is aligned with the compressible structural element. Detection takes place only within the range of the compressible structural element. Since the structural element is pressure-sensitive, a radial deformation of this takes place if the tire pressure changes. Consequently, there is a change in the material constant $£_r$. Because a phase difference between an incident wave (transmission signal) and a reflected wave (reflection signal) occurs when there is a change in the radial deformation of the compressible structural element, the current pressure of the tire can be concluded.

According to a further development of the invention, the compressible structural element is provided with a plurality of reflector elements on its outside, so that the detection of the radial deformation of the structural element can be improved. The reflector elements in the peripheral direction of the structural element are preferably metallized or comprise a metal material.

According to a further development of the invention, the transceiver unit is controlled by a control unit by means of a pseudorandom number generator, so that noise suppression between the transceiver units associated with each tire is ensured. This means that the probability of undesired interference between the transceiver units installed on the same or other vehicles is reduced.

According to an embodiment of the invention, the structural element is configured as a microwave cavity absorber, so that by determining a resonance frequency a change in the air pressure of the tire can be inferred. The object being measured is thus not a pressure-filled body. Advantageously, in this way signal processing can be made easier. Relatively low demands can be made on the flexible membranes integrated into the microwave cavity absorber regarding diffusion characteristics.

According to a further development of the invention, reflector elements can be arranged on the object being measured in the peripheral direction, oriented in different directions, preferably offset at 90° to one another, so that in addition a steering lock angle measurement of the wheel is guaranteed.

According to a further development of the invention, the transceiver unit comprises an additional antenna, the polarisation plane of which is rotated 90° to the antenna. In this way, two reflection signals can be detected simultaneously, so that firstly a tire pressure and secondly the steering lock angle measurement of the wheel are ensured.

According to a further development of the invention, the transceiver unit comprises a further antenna, aligned with a width of the rim and/or of the wheel, so that through the phase difference between the reflection signal and the transmission signal, a foreign body on or in the tire can be determined. Advantageously, it can thus be established if, by way of example, a nail has penetrated the tire.

Further advantages of the invention are indicated by the further subclaims.

Figure 2:
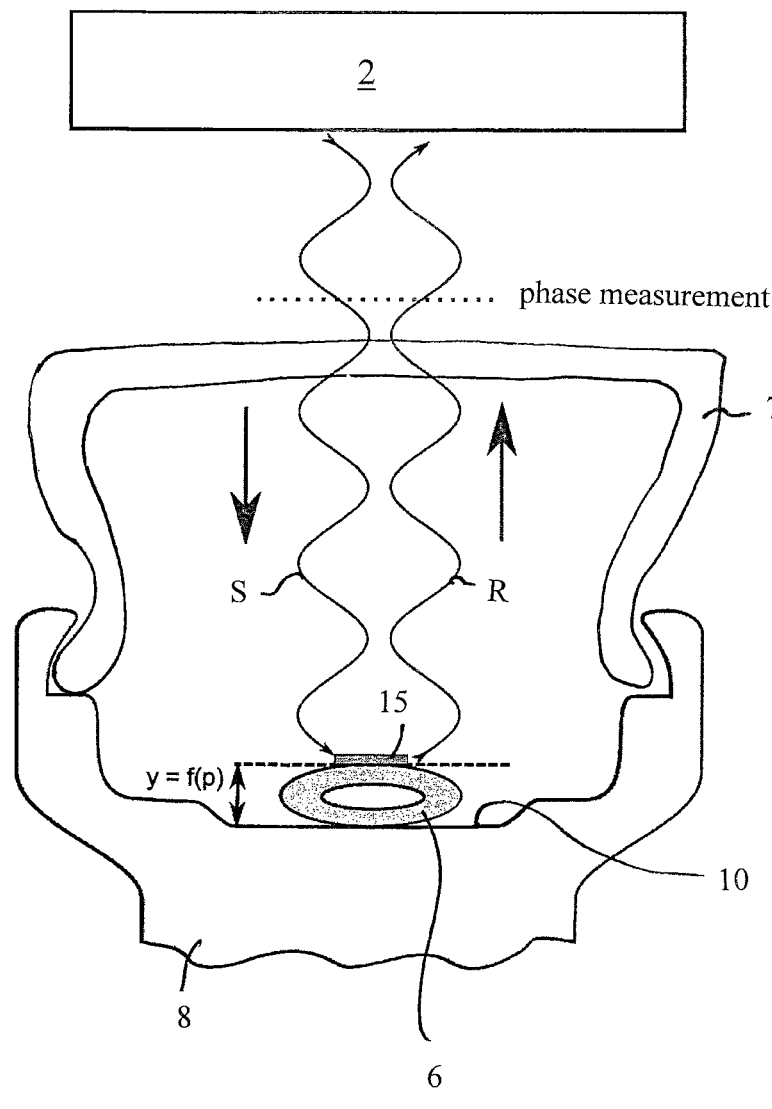
Figure 3:
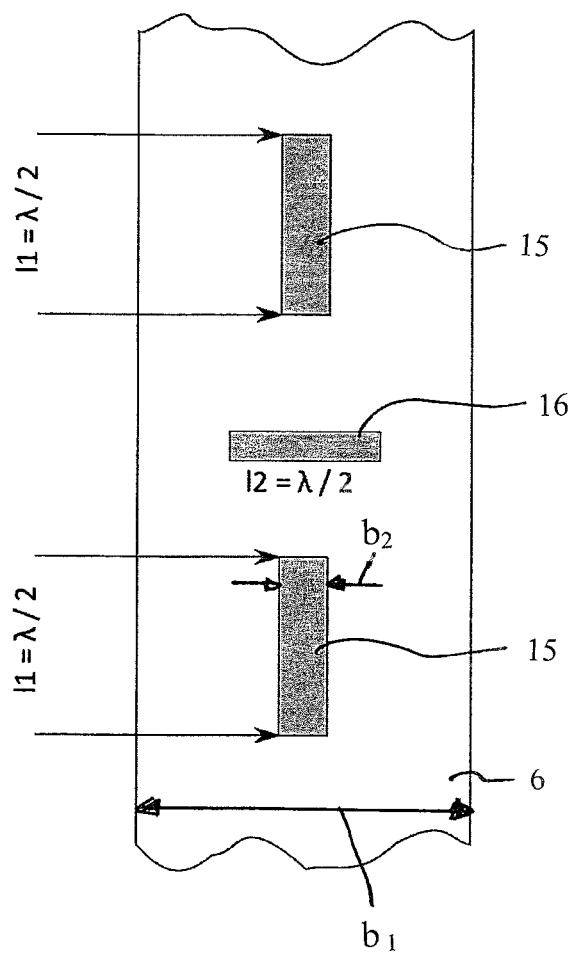
Figure 4:
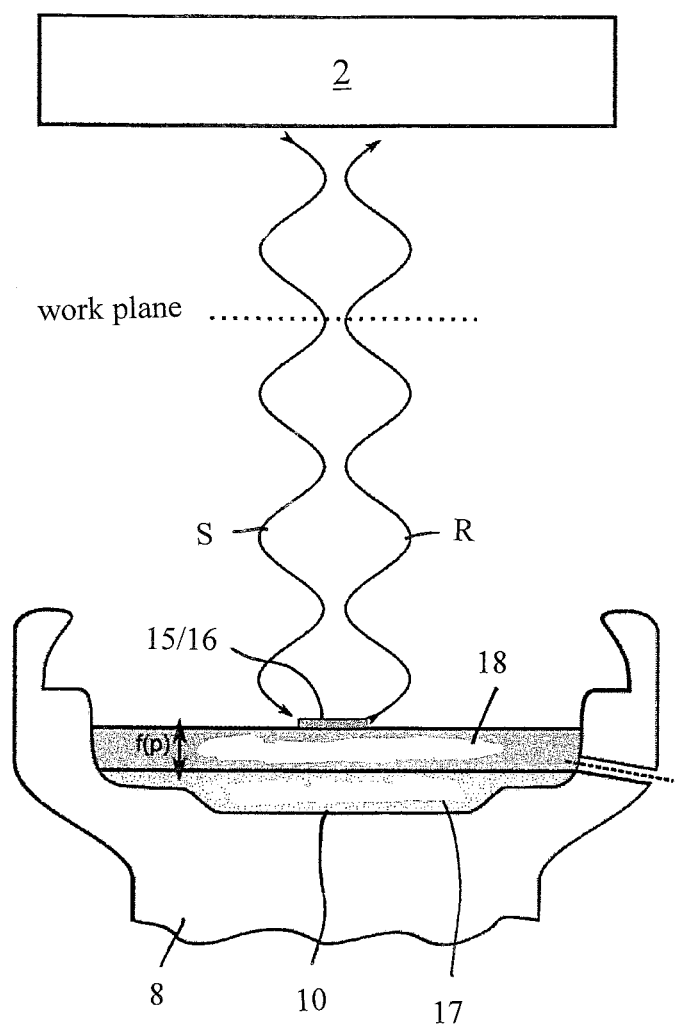
Figure 5:
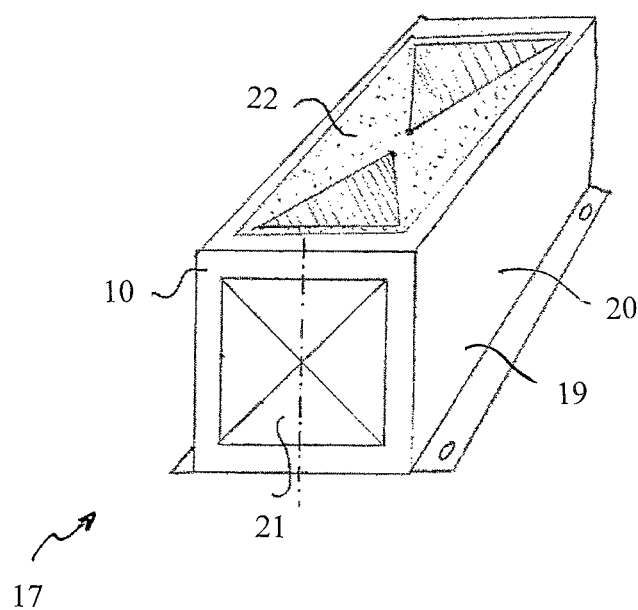
Figure 6:
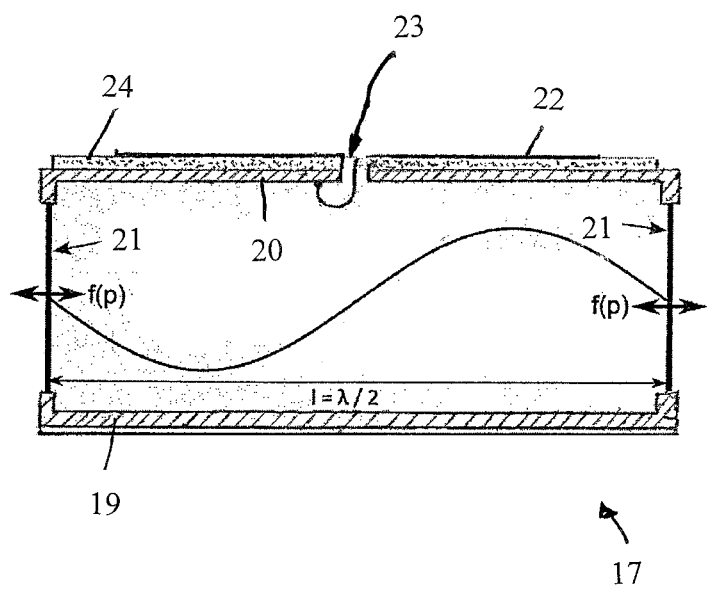

Exemplary embodiments of the invention are explained in more detail in the following using the drawings:

These show as follows:

FIG. 1 a schematic representation of a device according to the invention, arranged in a wheel arch or a wheel of a vehicle;

FIG. 2 a cross-section through a wheel with a compressible structural element integrated into a rim well, to determine a tire pressure of the wheel;

FIG. 3 a top view of a section of the of the compressible structure element according to FIG. 3;

FIG. 4 a cross-section through the wheel with a structural element configured as a microwave cavity absorber, arranged in the rim well to determine the tire pressure;

FIG. 5 a perspective view of the microwave cavity absorber;

FIG. 6 a side view of the microwave cavity absorber; and

Figure 7:
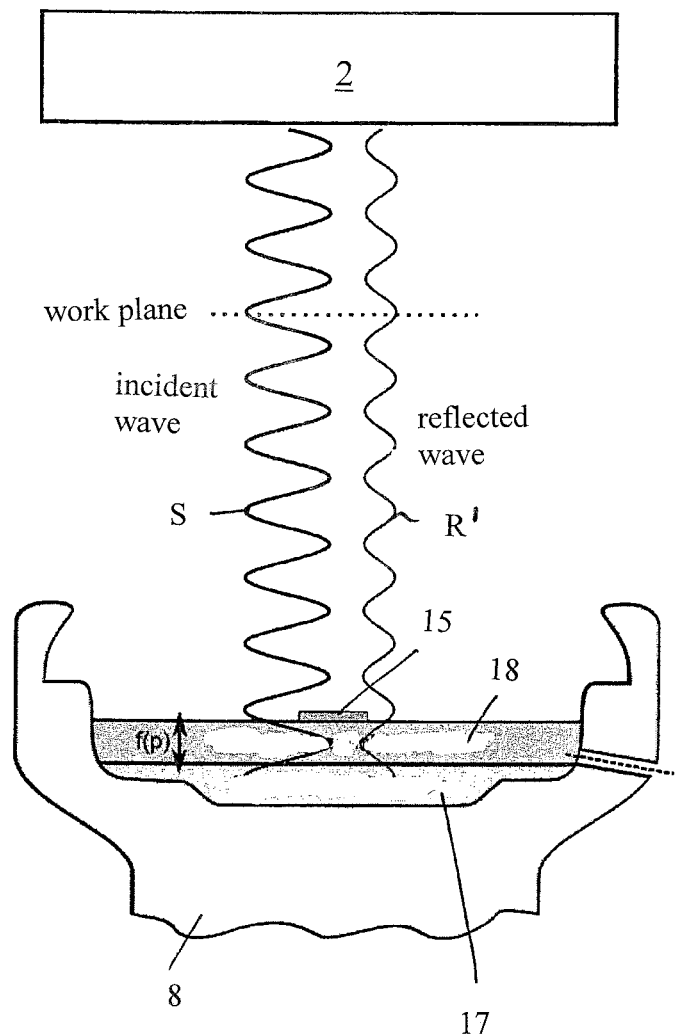

FIG. 7 a cross-section of the wheel wherein, unlike the measurement according to FIG. 4, the microwave cavity absorber is used for wheel parameter measurement.

A device for measuring and/or monitoring tire-related variables of a vehicle comprises a sensor unit 1, which essentially includes a transceiver unit 2, integrated into a wheel arch 3 of a vehicle (motor vehicle). The sensor unit 1 can be connected to a remotely arranged control unit 4, preferably arranged in the vehicle, via signal lines, by way of example a CAN-Bus. For measurement or monitoring of a tire pressure of a wheel 5 of the vehicle, a structural element 6 is arranged as the object being measured in an interior space 9 delimited by a tire 7 and by a rim 8 of the wheel 5.

According to a first embodiment of the invention in accordance with FIG. 2, the structural element 6 is configured as a compressible structural element, positioned or secured in a rim well 10 of the rim 8.

As indicated in FIG. 1, the transceiver unit 2 comprises a vector network analyser VNA, an analysis unit 11, a digital signal processor DSP arranged between the analysis unit 11 and the network analyser VNA, and an antenna unit 12 containing a transmitting/receiving antenna 13 and receiving antenna 14.

The network analyser VNA comprises an oscillator that generates a sinusoidal measurement signal in the microwave frequency range of, by way of example, 300 MHz-300 GHz, preferably between 6.0 and 8.5 GHz. The transceiver unit 2 has a microprocessor for signal processing and control and a bus circuit for cable-based data transmission via a bus connection with a decentralised or centralised remotely arranged control unit 4. The transceiver unit 2 preferably also has a DC-DC conversion unit. The network analyser VNA also comprises a processor and test ports, wherein the processor is connected via directional couplers with the test ports. The network analyser VNA can thus generate a transmission signal S, which is transmitted via the transmitting/receiving antenna 13 of the antenna unit 12 to the compressible structural element 6. By means of the transmitting/receiving antenna 3, a reflection signal R, reflected on the compressible structural element 6, is received and analysed in the analysis unit 11 by determining a phase difference between the transmission signal S and the reflection signal R.

To increase the measurement accuracy, the compressible structural element 6, configured as a circular endless hose, extending in the peripheral direction of the wheel 5 resting on the rim well 10, comprises on its outside a plurality of first reflector elements 15 oriented in the peripheral direction 15. These first reflector elements 15 are arranged at a distance from one another in the peripheral direction. The length of the first reflector elements 15 is determined by the working frequency or the frequency of the transmission signal S. Whereas the compressible structural element 6 can be configured as a rubber hose, the first reflector element 15 can be made from a metal material. The first reflector element 15 is made from a microwave-absorbent material. This means that the first reflector element 15 is significantly more apparent in the magnitude of the reflection measurement than the otherwise strongly reflecting background of the rim well 10. The reason for this is that at the frequencies for which the reflector element 15 has a length $l_1$ of approximately $\square/2$, the waves are primarily reflected by this. The proportion of reflected waves not reflected by this resonant first reflector element 15, is transmitted twice by the microwave-absorbent material 15 in its reflection against the rim well 10 and is accordingly damped. In this way, therefore, the rim reflection as disturbance can be considerably reduced. Furthermore, windowing can be simplified in this way and the effective signal-to-noise ratio increased. Furthermore, a precise determination is possible of the working frequency of the passive reflection element 15 in the magnitude of the S11 measurement. The requirements for the manufacturing precision of the reflector element 15 can be reduced in this way. From the local maximum of the S11 measurement, the exact frequency point for the phase measurement can be determined.

To this end, it is expedient for the transmitting/receiving antenna 13 to be aligned exclusively with the structural element 6 or the first reflector element 15. The maximum detection range in the axial direction is delimited by a width $b_1$ of the structural element 6. This condition applies if the tire pressure is measured exclusively with the structural element 6, and not with the first reflector element 15.

If the measurement of the tire pressure takes place including the strip-shaped reflector elements 15 arranged in the length $l_1$ of $\square/2$ on the structural element 6, the detection width of the transmitting/receiving antenna 13 is delimited by the width $b_2$ of the strip-shaped reflector elements 15. Advantageously, the sensor unit 1 in this variant is able to measure, in addition to the tire pressure, the speed of the wheel or the tire.

The sensor unit 1 is suitable for measuring the compression depth of the wheel 5. To this end a phase analysis is performed by the network analyser VNA.

The transceiver unit 2 sends a sinusoidal signal with frequency fi (i: running index) to the tire. On the surface of the tire, this sinusoidal signal is reflected to a not inconsiderable degree, i.e. beamed back. The transceiver unit 2 receives the reflected and phase-modified sinusoidal signal and analyses the phase $\varphi(fi)$. This measurement is performed at further frequencies. From the phase, via the transmission frequency, the proximity information can then be determined.

In the high-frequency and microwave range for the propagation in the clearance, the following propagation coefficient applies $$\beta(fi) = \beta i = (2\pi fi)/c0, \quad (1)$$

wherein c0 indicates the speed of light ([6]: Heuermann, H., Hochfrequenztechnik. *Lineare Komponenten hochintegrierter Schaltungen*, [High-frequency technology. Linear components of highly-integrated circuits] *Vieweg-Verla*, ISBN 978-3-8348-07969-4, $2^{nd}$ Ed. May 2009).

Thus, for the entire phase rotation of the reflection measurement over the distance lx for the frequency point fl at the input and at the recipient the following applies:

$$\text{Phase}(rg) = 2\beta 1 + rx, \quad (2)$$

wherein rx is the known reflection factor of the tire surface.

The phase is measured only in the uniqueness range of 360°. As a result, for the entire phase value of rg as a function of measured value of the phase of rm the following applies:

$$\text{Phase}(rg) = \text{Phase}(rm) + n \cdot 2\pi, \quad (3)$$

wherein n is a whole number, to be determined in due course.

The measured values of the reflection factor are present from a lower frequency flu to an upper frequency flo as a phase value of rum and rom. Between the various measurement points there should be no phase jumps, and these can easily be eliminated by practical mathematics.

From these two measured values and the known associated frequency points the phase slope can be determined via the frequency:

$$S = \text{delta}\_\varphi/\text{delta}\_f = (\text{Phase}(rom) - \text{Phase}(rom))/(flo - flu). \quad (4)$$

At the arbitrary frequency fi, due to the slope, there is a base phase rotation of $$\varphi i = fi\ S. \quad (5)$$

Equation (5) can also be derived with fo=fi and fu=0 Hz and the associated phase values from equation (4). With the following condition $$180° < \text{abs}(\text{Phase}(rim) + n \cdot 2\pi - fi\ S) \quad (6)$$

the correct value for n is found.

For the length determination, the distance lx based on equation (2) applies for each frequency point:

$$lx = (\text{Phase}(rg) - \text{Phase}(rx))/(2\beta 1). \quad (7)$$

Apart from the exact solution, rx can also be determined by a one-off measurement for a known length. In practice, equation (7) can be analysed for each measured frequency point, such that through a subsequent averaging process stochastic errors are minimized.

The precision of this measurement increases with the bandwidth (flo-flu) and the number of measurements.

The distance lx now calculated is proportional to the compression depth.

This value is subsequently also needed for the other measurements, as will be indicated in the "windowing" section below.

To determine the tire pressure the phase of the reflection signal R (S11-measurement) is compared with the phase of the transmission signal S. If the structural element 6, by way of example configured as a rubber hose, is not compressed, then there is significantly more rubber in the transmission path than in the compressed state. Through the changing quantity of dielectric material, the phase measurement results alter and are thus proportional to the pressure. The measurement of the deformation of the structural element 6 is simplified by the reflector elements 15 applied, since at the resonance frequency of the reflector elements 15 these can be specifically used for the phase measurement. In this way the accuracy of the measurement can be increased or the measurement accuracy demanded of the network analyser VNA reduced.

The dirt or other disturbances such as wheel rim reflection, phase rotation by tires, or moisture film on the housing of the transceiver unit 2, can change the transmission characteristics in magnitude and phase. This disturbing effect can be eliminated by windowing for all measurements. To this end analysis means are provided, so that the reflection signal R through inverse Fourier transformation is transformed in the time range, and then the known time ranges (surface of the housing is a given and fixed and the tire distance has been measured) are windowed out and then the S11-signal filtered in this way is transformed back into the frequency range by discrete Fourier transformation. The complex reflection behaviour that results on the surface of the rim 8 is now the dominant signal. This process is only possible by determination of the measured values by magnitude and phase, e.g. vectorially.

According to a further embodiment of the invention, the compressible structural element 6 can also have two reflector elements 16, arranged in the axial direction of the tire 7 or the rim 8. The second reflector elements 16 are thus arranged perpendicularly to the first reflector elements 15 or have the same length $l_2 = \square/2$ as the first reflector elements 15. Since they are rotated by 90°, a horizontal position and, by means of the first reflector elements 15, a vertical position are guaranteed. In this way, a lock angle of the wheel 5 can also be measured.

According to a further embodiment of the invention in accordance with FIG. 4, instead of a compressible structural element 6 a microwave cavity absorber 17 can be provided that can be covered by an open-pore foam layer 18, on the outside of which the quantity of first reflector elements 15 and/or second reflector elements 16 is arranged. The microwave cavity absorber 17, like the foam layer 18, is arranged circularly. The microwave cavity absorber 17 lies directly in the rim well 10 of the rim 8. As clearly shown in FIGS. 5 and 6, the microwave cavity absorber 17 has a housing 19 containing a longitudinal wall 20, extending in a circular manner along the rim well 10. The microwave cavity absorber 17 extends in a part-circular manner in the peripheral direction, wherein the distance between the two membranes 21 with flexible ends is given by the resonance frequency. The length l of the microwave cavity absorber 17 is thus $\square/2$. On a side of the housing 19 turned away from the rim well 10 an antenna 22 extends along the outside of the longitudinal wall 20. The antenna 22 is in contact via a slot 23 in the longitudinal wall 20 with an inside of the longitudinal wall 20. The antenna 22 is secured via an insulation 24 to the longitudinal wall 20 of the housing 19. A pressure-dependent microwave resonator is hereby provided, the resonance frequency of which is dependent on the pressure of the tire 7. The flexible membranes 21 can, by way of example, be in the form of a biaxially oriented polyethylene terephthalate material or film (bo-PET, Mylaer). The antenna 22 is configured as a planar antenna.

In order that this measurement system has the necessary crosstalk insulation between the transmission signal and the receiver, it is necessary to perform a one-off system error correction during production, as is the case with any commercially available VNA. This must be performed in the clearance, however. Methods to be considered here are published in the document: "Heuermann, H., *Sichere Verfahren zur Kalibrierung von Netzwerkanalysatoren für koaxiale and planare Leitungssysteme*, [Methods for calibrating network analysers and planar control systems], *Dissertationsschrift* [Dissertation], Institut für Hochfrequenztechnik, Ruhr-Universität Bochum, 1995, ISBN 3-8265-1495-5)".

The LNN two-factor method is preferably used. Alternatively, from the S-3-R method described, an M-3-R method can be derived, which can similarly be used for clearance measurements.

In the M-3-R method, four single-port measurements are performed:
1) M-measurement: antenna directed towards the sky (or absorber).
2) 3-R-measurements: The reflection on a triple mirror is measured in 3 positions at known distances.

From these calibration measurements, for each frequency point the 3 complex error coefficients of the 3-term method are calculated. With these 3 complex error coefficients or terms, the measured values are corrected and, inter alia, the crosstalk between transmission and reception path are calculated from these.

This VNA calibration must be carried out before windowing as described.

According to a further embodiment of the invention in accordance with FIG. 7, the transceiver unit 2 can also be used to send and receive a transmission signal S in frequencies outside of the working range of the microwave cavity absorber 17 for wheel parameter measurement. The microwave cavity absorber 17 damps the reflection signal R' of these frequencies with respect to the resonator reflection. Thus, the resonators can be found more easily in the measurement results.

The first reflector elements 15 and the second reflector elements 16 enable during straight running of the wheels (no steering lock) just the reflections of the first reflector elements 15 to be detected. With a steering lock, additional reflections on the second reflector elements 16 occur. With a steering lock of 45° the reflection components of the first reflector elements 15 and the second reflector elements 16 are the same.

For measuring the steering lock, the transceiver unit 2 can alternatively also have the additional receiving antenna 14, the polarisation plane of which is rotated by 90° to the receiving antenna 13. During straight running the antenna 14 receives no signal. With increasing steering lock, the signal of the receiving antenna 14 becomes greater and on the receiving antenna 13 smaller. The direction, whether steering left or right, is obtained from the phase difference between the two reflection signals R determined for the first receiving antenna 13 and the second receiving antenna 14.

If it is intended that the sensor unit can detect foreign bodies in or on the tire 7, the entire width of the tire 7 must be detected. The transmitting/receiving antenna 13 must have a directional characteristic, such that on the one hand it covers the entire width of the tire and on the other detected segments in the peripheral direction of the tire 7 are as narrow as possible. Thus, scanning of the tire 7 in the peripheral direction can take place. In the presence of a foreign object, by way of example a nail, in a segment of the tire 7, a reflection value R results that is different from the other segments of the tire 7 detected in the peripheral direction.

Control of the sensor unit 1 preferably takes place by means of a random number generator, so that the transceiver units 2 associated with each of the wheels 5 are controlled with a time shift and mutual interference is avoided.

The invention claimed is:

1. A device for measuring and/or monitoring tire-related variables of a vehicle with a sensor unit (1) for transmitting, receiving and processing signals, comprising
an antenna unit of the sensor unit (1) for emission of a transmission signal (S) in the direction of an object being measured (7) and wherein a reflection signal (R, R') reflected by the object being measured is received and analysed, and
a transceiver unit (2) of the sensor unit (1), by means of which a reflection factor (S11), formed as the quotient from the reflection signal reflected by the object being measured (R) and the transmission signal (S), is measured, and by means of which a resonance frequency and/or a phase difference between the transmission signal (S) and the reflection signal (R) is determined,
wherein the transceiver unit (2) has a vector network analyser (VNA) and an analysis unit (11), so that a distance to the object being measured (7) is established by detecting the phase difference between the transmission signal (S) and the reflection signal (R), and
wherein first reflector elements (15) oriented in the peripheral direction and second reflector elements (16) arranged transversally to the first reflector elements (15) are provided, so that the reflection signal (R') is varied as a function of a steering lock of a wheel (5).

2. The device according to claim 1, wherein the phase difference is determined for a plurality of identical and/or different frequency values and/or in a specified bandwidth and wherein the object being measured is a tire (7), so that from the distance determined between transceiver unit (2) and the tire (7) a compression depth of the tire (7) is determined.

3. The device according to claim 1, wherein the analysis unit (11) has analysis means, so that the reflection signal (R) and inverse Fourier transformation existing with magnitude and phase are transformable in the time range, in a signal processor of the transceiver unit (2) a time range, determined by the position thereof and distance thereof from the object being measured, is windowed, and the filtered reflected signal (P) through Fourier transformation can be transformed back into the frequency range.

4. The device according to claim 1, wherein the sensor unit (1) is controlled via a pseudorandom number generator, so that transceiver units (2) associated with each of a plurality of wheels (5) is impinged upon with a time shift.

5. The device according to claim 1, wherein the transmitting/receiving antenna (13) of the transceiver unit (2) is aligned with a width ($b_1$, $b_2$) of a rim (8) and/or of the tire (7), so that through the phase difference between the reflection signal (R) and the transmission signal (S) a foreign body in the tire (7) is detected.

6. A device for measuring and/or monitoring tire-related variables of a vehicle with a sensor unit (1) for transmitting, receiving and processing signals, comprising
an antenna unit of the sensor unit (1) for emission of a transmission signal (S) in the direction of an object being measured (7) and wherein a reflection signal (R, R') reflected by the object being measured is received and analysed, and
a transceiver unit (2) of the sensor unit (1), by means of which a reflection factor (S11), formed as the quotient from the reflection signal reflected by the object being measured (R) and the transmission signal (S), is measured, and by means of which a resonance frequency and/or a phase difference between the transmission signal (S) and the reflection signal (R) is determined,
wherein the transceiver unit (2) has a vector network analyser (VNA) and an analysis unit (11), so that a distance to the object being measured (7) is established by detecting the phase difference between the transmission signal (S) and the reflection signal (R), and wherein the transceiver unit (2) is arranged in a wheel arch (3) of a vehicle and wherein the wheel (5) comprises a compressible structural element (6), which is arranged within an interior space (9) delimited by a tire (7) and a rim (8) of a wheel (5) in the peripheral direction of the wheel (5), and wherein the antenna unit (12) of the transceiver unit (2) is aligned with the structural element (6).

7. The device according to claim 6, wherein the compressible structural element (6) is configured as a circular endless tube, arranged in a rim well (10) of the rim (8) and/or secured to this.

8. The device according to claim 7, wherein on the rim well (10) as the object being measured, there is a pressure-dependent microwave cavity absorber (17) with a housing (19) containing a longitudinal wall (20), to which an antenna (22) is secured, and containing flexible membranes (21) arranged on the opposite sides of the longitudinal wall (20), so that by determining a resonance frequency an air pressure of the tire (7) is inferred.

9. The device according to claim 6, wherein the compressible structural element (6) is provided with a plurality of reflector elements (15, 16) on its outside.

10. A device for measuring and/or monitoring tire-related variables of a vehicle with a sensor unit (1) for transmitting, receiving and processing signals, comprising an antenna unit of the sensor unit (1) for emission of a transmission signal (S) in the direction of an object being measured (7) and wherein a reflection signal (R, R') reflected by the object being measured is received and analysed, and a transceiver unit (2) of the sensor unit (1), by means of which a reflection factor (S11), formed as the quotient from the reflection signal reflected by the object being measured (R) and the transmission signal (S), is measured, and by means of which a resonance frequency and/or a phase difference between the transmission signal (S) and the reflection signal (R) is determined, wherein the transceiver unit (2) has a vector network analyser (VNA) and an analysis unit (11), so that a distance to the object being measured (7) is established by detecting the phase difference between the transmission signal (S) and the reflection signal (R), and wherein the transceiver unit (2) comprises an additional antenna (14), the polarisation plane of which is rotated 90° to the antenna (13), such that from the phase difference of reflection signals (R) detected by these two antennas a steering lock of a wheel (5) is determined.

* * * * *